United States Patent
Cai et al.

(10) Patent No.: US 12,220,556 B2
(45) Date of Patent: *Feb. 11, 2025

(54) PUMP FOR IMPLANTABLE MEDICAL DEVICES

(71) Applicant: CraniUS LLC, Baltimore, MD (US)

(72) Inventors: John Cai, Baltimore, MD (US);
Nathan Scott, Baltimore, MD (US);
Charles Watkins, Baltimore, MD (US);
Ashley Hinga, Baltimore, MD (US);
Elayna Williams, Baltimore, MD (US);
Charlotte Quinn, Baltimore, MD (US);
Mark Gonzales, Baltimore, MD (US);
Owen Friesen, Baltimore, MD (US);
Conner Delahanty, Baltimore, MD (US)

(73) Assignee: CraniUS LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,051

(22) Filed: Oct. 6, 2023

(65) Prior Publication Data

US 2024/0075203 A1     Mar. 7, 2024

Related U.S. Application Data

(63) Continuation of application No. 18/309,138, filed on Apr. 28, 2023, now Pat. No. 11,813,429.
(Continued)

(51) Int. Cl.
*A61M 5/142* (2006.01)
*A61M 31/00* (2006.01)

(52) U.S. Cl.
CPC .... *A61M 5/14276* (2013.01); *A61M 5/14224* (2013.01); *A61M 31/002* (2013.01);
(Continued)

(58) Field of Classification Search
CPC .......... A61M 5/14276; A61M 5/14224; A61M 31/002; A61M 2205/0272;
(Continued)

(56) References Cited

U.S. PATENT DOCUMENTS

| | | | |
|---|---|---|---|
| 3,923,426 A | 12/1975 | Theeuwes | |
| 7,134,849 B1 | 11/2006 | Steck et al. | |
| 11,813,429 B1 * | 11/2023 | Cai | A61M 5/14276 |

OTHER PUBLICATIONS

International Search Report and Written Opinion issued on Aug. 23, 2023, in corresponding International Application No. PCT/US2023/070388, 9 pages.

* cited by examiner

*Primary Examiner* — James D Ponton
(74) *Attorney, Agent, or Firm* — Maier & Maier, PLLC

(57) ABSTRACT

A bidirectional electroosmotic pump may be provided. The bidirectional electroosmotic pump may be made of materials that are biocompatible and non-ferrous. The bidirectional electroosmotic pump may be part of an implantable medical device for the purpose of medicine delivery. The bidirectional electroosmotic pump may contain a working fluid and may facilitate the delivery of a separate payload fluid. In an exemplary embodiment, the bidirectional pump may contain bellows which may allow the pump to deliver the payload fluid through a series of valves and/or catheters. In another embodiment the bidirectional electroosmotic pump may contain a pump sensing mechanism to monitor the state of the pump.

15 Claims, 13 Drawing Sheets

Related U.S. Application Data

(60) Provisional application No. 63/404,237, filed on Sep. 7, 2022.

(52) U.S. Cl.
CPC ............... *A61M 2205/0272* (2013.01); *A61M 2205/3327* (2013.01); *A61M 2205/50* (2013.01)

(58) Field of Classification Search
CPC ...... A61M 2205/3327; A61M 2205/50; A61M 39/02; A61M 2005/14513; F04B 43/0736; F04B 23/00; F04B 17/03; F04B 19/006
See application file for complete search history.

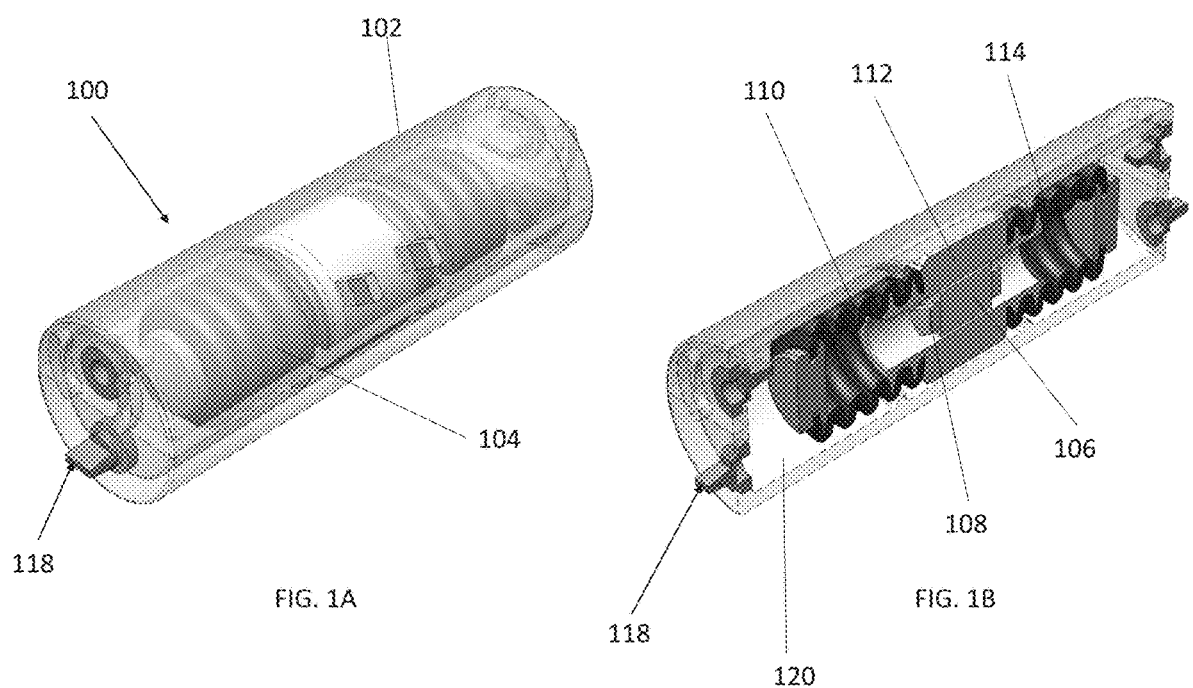

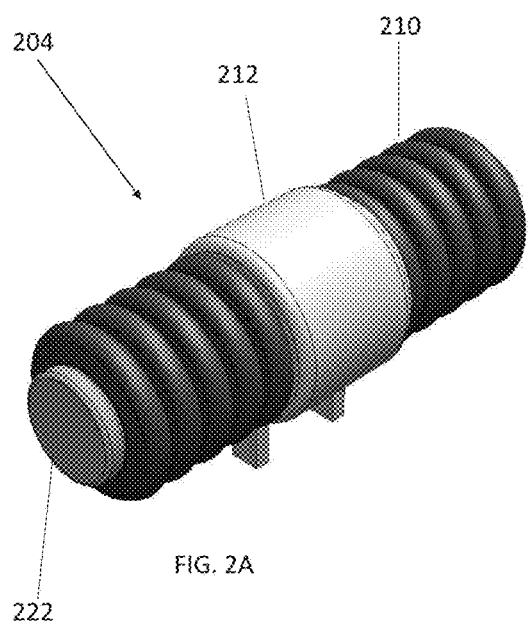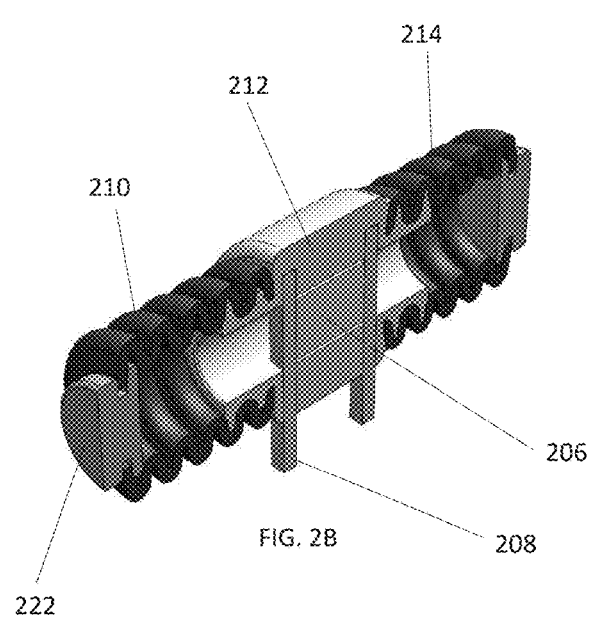

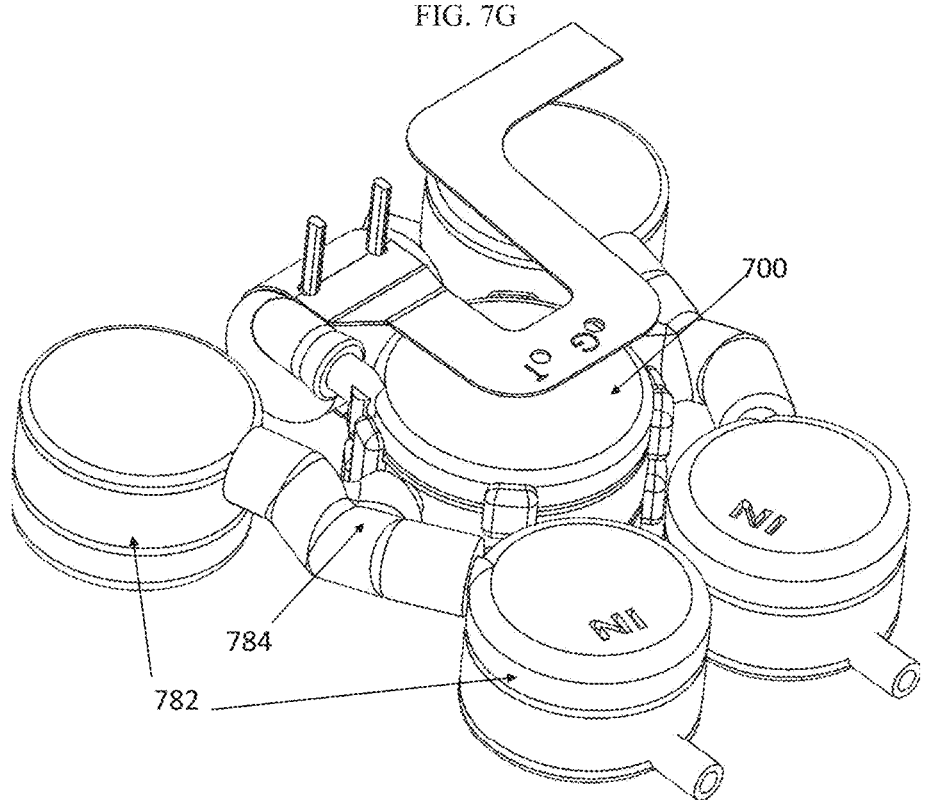

PUMP FOR IMPLANTABLE MEDICAL DEVICES

CROSS-REFERENCE TO RELATED APPLICATIONS

The present patent application is a continuation of U.S. patent application Ser. No. 18/309,138, filed on Apr. 28, 2023, which claims benefit and priority to U.S. Provisional Application No. 63/404,237, filed on Sep. 7, 2022, and which is hereby incorporated by reference into the present disclosure.

BACKGROUND

The use of implantable drug delivery devices has reduced required and/or repetitive surgeries, successfully targeted specific areas of the body, thereby increasing drug safety and efficacy, and eased the process of providing lifesaving medicine that was ineffective when delivered systemically; such as when surgical cancer resection is deemed impossible, suboptimal, and/or less effective, like with chronic disease management and/or when systemic/oral medicine dosing is ineffective in crossing a homeostatic cellular barrier (e.g. blood brain barrier) and reaching the targeted organ or tissue (e.g. brain). A key benefit of these implantable devices is the ability to precisely control and monitor how much of a medicine is being introduced to a specific body part and/or targeted organ. As a result, there is a serious concern and critical need to ensure that implantable drug delivery devices maintain a consistent dosage during delivery and that over/under delivery of medicine is avoided; since the goal is to optimize target organ delivery while minimizing or avoiding altogether toxicity risks and collateral damage to accessory, non-targeted organs. As such, the biocompatible pumps contained within these implanted devices play an important role in reliably delivering medicine in instances when other delivery routes such as oral or intravenous delivery are ineffective.

Currently, some implantable pumps used for patient disease management fail to provide a consistent and appropriate dosage under various environmental conditions, such as when the pump is within or near a magnetic resonance imaging (MRI) machine (e.g. they suffer loss of safe and dependable function after being within an MRI environment), with which the pumps are incompatible and unsafe. In other medicinal pumps, the internal components can react harshly with the medicine, resulting in serious malfunctions (e.g. viscosity issues leading to valve clogging), while other pump designs can mechanically fail over time given, for example, the repetitive movements required (e.g. peristaltic pump mechanisms with ball bearings). Furthermore, some medicinal pumps can have high power requirements that require large batteries and limit functional life (i.e. necessitating a repeat surgery every 3-7 years), while others cause visible deformity when placed in-situ under one's skin and soft tissue given their poor shape and design incompatible with the time-tested, methodical principles and practice of Neuroplastic Surgery (e.g. having sharp, firm, metal angles which cause unsafe pressure points underneath the skin leading to pain and focal ischemia). Because most implantable pumps on the market today contain some form of ferrous material, they cannot be effectively used in MRI settings. These issues can result in premature pump failure (e.g. metal corrosion), image distortion resulting in poor diagnostic information (i.e. failing to be MRI-lucent), poor patient satisfaction (e.g. by inhibiting a patient from entering a MRI machine, which can severely limit the diagnostic capabilities available for definitive treatment decisions), impaired quality of life (e.g. by preventing MRI-treatment procedures for pain relief, which can be combined with MRI imaging), premature removal of the pump halting delivery altogether (e.g. when premature mechanical failure can only be addressed with additional surgery), and/or patient death if high concentrations of medicine are delivered unexpectedly all at once above the therapeutic range (e.g. documented cases of peristaltic pumps having overdosage post-MRI thereby leading to severe consequences and major risk related to patient safety).

Implantable medical devices designed to deliver medicine to the body are commonly large metallic objects that contain ferrous material. These devices use conventional pumps, such as syringe pump mechanisms or peristaltic pump mechanisms which rely on bulky, ferrous, and power-hungry motors. Electroosmosis is a commonly used mechanism in scientific research for microfluidic delivery of precise and low flow rates. There are very few commercially available electroosmotic pumps (EOPs), and only for direct transfer, or delivery, of a working fluid (WF) in a unidirectional flow pattern, thereby limiting their use and delivery options to a limited set of liquids.

SUMMARY

According to at least one exemplary embodiment, an electroosmotic pump may be provided. The electroosmotic pump may be made of a variety of materials that are biocompatible and non-ferrous. The electroosmotic pump may be part of an implantable medical device. The electroosmotic pump may contain a chamber that contains a working fluid. The electroosmotic pump may be designed to provide bidirectional flow to permit pumping a payload fluid which is different than the working fluid. In an exemplary embodiment, the pump may contain bellows which may allow the pump to deliver the payload fluid through a series of valves and/or catheters. These bellows may be made of, for example, titanium (or other inert, durable material). In another embodiment the electroosmotic pump may contain a pump sensing system to monitor the state of the pump.

According to at least one exemplary embodiment, a method of using an electroosmotic pump may be provided. The method of using the electroosmotic pump may include moving a working fluid back and forth between an electroosmotic element housing and a bellows assembly by applying alternating polarity electric potential to an electroosmotic element through one or more electrodes. The reciprocating movement of the working fluid may drive two or more independent bellows which may dispense a payload fluid from the electroosmotic pump. This reciprocating movement may provide bidirectional flow and opposing vectors of medicinal catheter flow. Having at least two catheters per EOP, instead of one catheter per EOP, may add an additional layer of duplicity which is invaluable when delivering medicine; given that one catheter could become obstructed unexpectedly in the setting of physiological scar tissue development towards the end of one of the catheters. This may allow for continued delivery of medicine without interruption and may also shrink the potential footprint.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 1A shows a first exemplary embodiment of an electroosmotic pump that is designed with bi-directional flow that can minimize both the overall footprint of a device as well as the area required within the human body for implantation.

FIG. 1B shows a cross-sectional view of an exemplary embodiment of a bidirectional electroosmotic pump.

FIG. 2A shows an exemplary embodiment of an inner assembly of a pump.

FIG. 2B shows a cross-sectional view of an exemplary embodiment of the inner assembly of the pump.

FIG. 7G shows an exemplary bidirectional electroosmotic pump assembly with check valves.

DETAILED DESCRIPTION

Figure 1C:
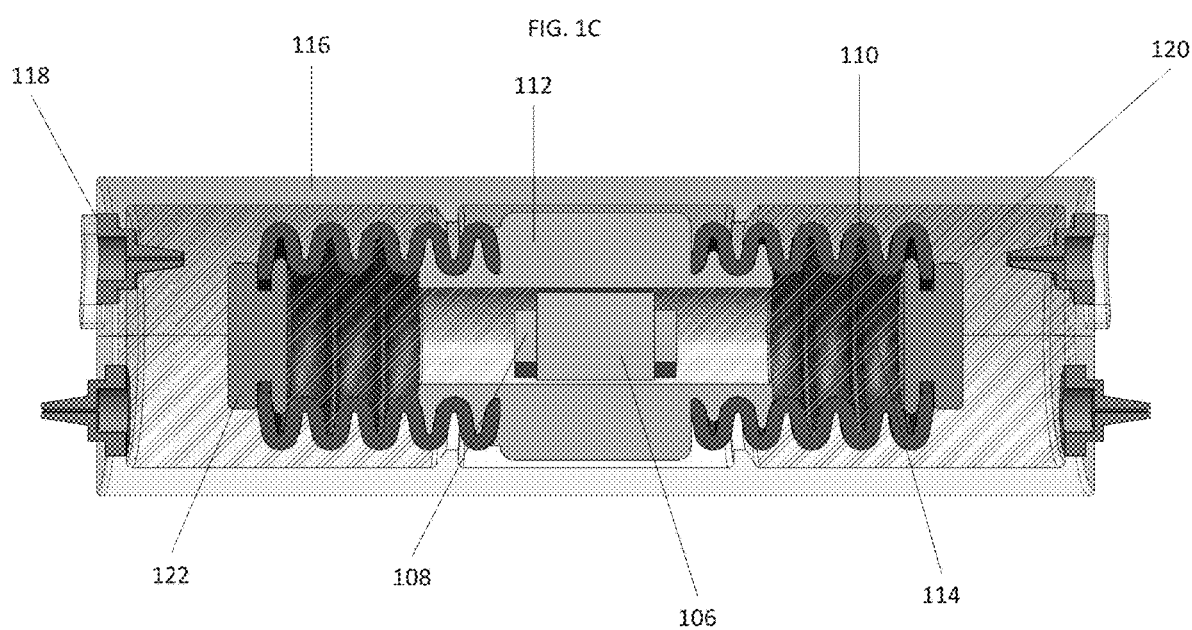
FIG. 1C shows a cross-sectional view of an exemplary embodiment of the parts of the bidirectional electroosmotic pump.

Aspects of the invention are disclosed in the following description and related drawings directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

As used herein, electroosmotic element (EOE) means a structure that has a working fluid move through when a voltage is applied across the structure. Because the fluid moves towards the negative terminal, by alternating the polarity of the applied voltage the electroosmotic element can create reciprocating fluid motion.

As used herein, a bidirectional electroosmotic pump (EOP) means a structure that uses an EOE with an alternating polarity to drive a payload fluid, at a precise and low flowrate, in two directions.

FIG. 1A depicts an embodiment of an electroosmotic pump device 100 with an external housing 102 surrounding an inner assembly 104. It may be appreciated that the internal elements may be formed out of any of a variety of materials or combinations thereof, based on implementation and use. Further, in the embodiments, the components utilized in the pump assembly may be biocompatible with the human body and may be absent of any ferrous-containing elements, which can mitigate adverse effects related to MRI equipment or imaging conditions and allow the device to be both MRI-compatible and devoid of any radiological artifact. Thus, in some further embodiments, the embodiments may include a pump, or pumps, that are MRI-safe (i.e. the device, when used in the MRI environment, presents no additional risk to the patient or other individual, but it may affect the quality of the diagnostic information), MRI-compatible (i.e. a device that is MRI safe when used in the MRI environment, to neither significantly affect the quality of the diagnostic information nor have its operations affected by the MRI system), and/or MRI-lucent (i.e., a device that is MRI compatible and when used in the MRI environment, is radiographically invisible on MR imaging and thereby able to prevent unwanted artifact and prevent the risk of suboptimal MR imaging value for pathology assessment). The external housing 102 may be cylindrical or, in other embodiments, adjusted to a different shape which is lower profile for human body implantation to avoid any visible deformity when placed under skin and soft tissue. The external housing 102 of the device may be formed from a biocompatible and durable plastic or photocured resin or any other safe and sterilizable material that is FDA-approved for reconstructive purposes. For example, the external housing 102 may be formed from any alloplastic material or paramagnetic material (i.e. titanium) capable of human use and compatible with the working fluid and payload fluid. Other shapes and/or materials may be used based on the use and implementation of the pump for certain disease conditions and anatomical variance (i.e. placement within head, chest, abdomen, joint space, and/or extremity, as desired). Each end of the external housing 102 may include one or more valves 118 to facilitate the flow of a payload fluid 120 without backflow. The one or more valves 118 may be, for example, duckbill valves, and may be formed from silicone, Viton, fluorosilicone, or another MRI-lucent material. In an exemplary embodiment, the valves 118 may be duckbill valves, which may support an effective low flow rate system because of the small amount of pressure required to open them and the lack of resistance created by the valves 118. Other types of valve systems may include, but are not limited to, diaphragm valves, custom valve flaps, umbrella valves, or other flow metering systems, as desired. In an exemplary embodiment, there may be a set of four valves, two of which facilitate the flow of fluid into the pump and two of which facilitate driving fluid out of the pump. In other embodiments, there may be fewer valves utilized, which may be accomplished, for example, by combining fluid channels so there is one inlet and one outlet valve. It may be understood that in other embodiments, only two valves may be used, or more or less than four valves may be used, depending on application. In an embodiment, a bi-directional pump may be desired over a uni-directional pump, because the bi-directionality may enable the delivery of a payload fluid, such as, for example, a medicine to be directly delivered to the brain or targeted body part, that is different than the working fluid within the EOP. Further, the added duplicity of two catheters per pump (versus one catheter per pump) may mitigate instances of unexpected catheter blockage secondary to normal physiologic scar tissue following placement, which may be a safer and more effective option for chronic medicine delivery.

FIG. 1B depicts an embodiment of the cross-sectional view of the device inner assembly 104 with parts of the inner assembly shown. In an embodiment, the inner assembly 104 may contain the electroosmotic element 106 which may be contained by a holder 112 and may receive a voltage from electrodes 108. The holder 112 can be connected to bellows 110 which can contain a working fluid 114. External to, or surrounding, the inner assembly 104 there may be the payload fluid 120 which may be contained by the external housing 102. It should be understood that this is merely an exemplary configuration and, depending on application or location of an implant, different configurations may be used. In addition, the bellows can be shaped and designed with various forms to improve long-term conditions, enhance function, and/or minimize wear, tear, or degradation.

FIG. 1C depicts a cross section of an embodiment of the electroosmotic pump device 100, with internal elements of the bidirectional pump shown. It may be appreciated that the internal elements may be formed out of any of a variety of materials or combinations thereof, based on implementation and use. In an embodiment, the electroosmotic device 100 may include an electroosmotic element 106 that may be formed by, for example, using a ceramic cylinder, or another porous material, and which may be contained by a holder 112, which may be formed, for example, with high-density polyethylene (HDPE), polyphenylene sulfide, polycarbonate, photocuring resin, or another material or set of materials that can bond around the external surface of the electroosmotic element. In an exemplary embodiment, a ceramic element may be incorporated to avoid any ferrous materials and to assure MRI compatibility and/or MRI lucency. This may allow the pump(s) and/or any implanted devices using the pump(s) to increase long-term patient safety and enhance pump functionality, for example with respect to MR imaging conditions, especially in instances where the patient's disease, like chronic brain or spine diseases, requires serial MR imaging. The electroosmotic element 106 may be porous, which may enable the working fluid to flow through, causing the electroosmotic effect that drives the bidirectional electroosmotic pump.

Still referring to FIG. 1C, on either side of the electroosmotic pump 100 may be electrodes 108, which may be formed of platinum or another conductive material in order to produce a voltage differential to move the working fluid through the electroosmotic element. Platinum, in an embodiment, may be utilized for favorable material properties with respect to, for example, ductility and chemical inertness. In an embodiment, platinum may be utilized because it can interact with various working fluids while remaining inert. Further, the platinum may be formed into a desirable shape while maintaining electrical contact with the electroosmotic element 106. Other, non-platinum, materials may develop an oxidation layer when an electrical charge is applied thereby reducing the conductivity of the material and resulting bidirectional electroosmotic pump performance. The electrodes 108 may deliver a voltage to the electroosmotic element 106 that can cause pumping actuation to occur. The electroosmotic element holder 112 may be connected to each bellows 110, which may be positioned on either side of the holder 112, and which may be capped by plugs 122. The bellows 110 may be formed from titanium, silicone, fluoroelastomers, or other elastic materials such as latex that are compatible with the working fluid and the plugs 122 may be formed from resin, as desired. The bellows 110 shape in the embodiments may be such that it may minimize size, maximize function, and/or reduce long-term degradation associated with frequent or repetitive movements or from long-term contact with the working fluid and payload fluid as may be required in use in some embodiments. The plug can be made from resin printing, silicone, plastics, or another material which may reliably bind to the bellows 110. The plugs 122 can also be drilled so as to allow for filling with the working fluid 114, and then may be resealed with additional resin and UV curing. The bellows 110 may contain a working fluid 114 which may facilitate the deformation of the bellows 110. This working fluid 114, in an exemplary embodiment, may be strategically chosen based on its safety profile, polarity, it being a dielectric (which means a polarizable insulator), compatibility with the surrounding materials, such as the bellows, EOE, and holder, and/or its stability over time with respect to bubble formation, and may be, but is not limited to, ethanol, DI water, or dimethyl sulfoxide (DMSO). In other embodiments the working fluid 114 may be another polar fluid compatible with the pump materials, and some embodiments may require the working fluid 114 to be particle free, as particles in the working fluid 114 may clog the pores in the EOE, which may prevent the movement of the working fluid 114, which may reduce flow rate or cease pumping entirely. In some embodiments the fluid may have a viscosity similar to water, and the fluid may be sterilized with a method compatible with the bidirectional pump. For example, with ethylene oxide sterilization. Surrounding the holder 112 and the bellows 110 may be a casing 116 (for example formed of resin) that can contain an inner assembly 104 and the payload fluid 120. On each end of the casing 116 there may be two valves 118, for example formed of silicone, which can facilitate flow of the payload fluid 120 in and out of the electroosmotic pump 100.

FIG. 2A depicts an exemplary embodiment of the inner assembly 204. It may be appreciated that the parts may be formed out of any of a variety of biocompatible materials or combinations thereof for human body implantation, based on implementation and desired use, and/or for implantation in various animals. In this embodiment, the bellows 210 may extend from either end of the holder 212 and can be capped 222 to prevent the working fluid 214 from escaping. In this embodiment, the elastic design of the bellows 210 may facilitate their expansion and contraction in a precise manner so as to prevent over or under delivery of medicine, which could result in impaired patient safety, adverse drug events, and/or patient death. For example, the bidirectional pump may facilitate a flow rate of 0.5-5 µl/min, which may be desirable for specific applications including convection-enhanced delivery (CED). It may be appreciated that another configuration of the bellows 210 and their plugs may be used, depending on the implementation or packaging of the implant. Furthermore, in an embodiment, a sensor located inside of the implant may be utilized to provide, for example, an embedded biosensing system and/or data as to when the bellows 210 are in use or operation, maximally/partially flex and maximally/partially unflex, and also to alert a patient and/or healthcare provider of improper pump function with enhanced safety alarms. In other embodiments, custom rubber domes may replace the bellows 210 and plugs. In such an embodiment, the state of the pumping cycle can be detected using, for example, IR LEDs and phototransistors to determine the extent of deformation or expansion. Based on the reading, the pump can alternate flow direction. Another alternative embodiment may include custom conductive rubber domes which can be formed into various shapes. The conductive diaphragms may come into contact with the electrodes 208 and send signals to alternate the polarity. Further alternate embodiments could include latex coated in graphene, or a fluid barrier where a fluid membrane is used instead of a physical piece. This fluid membrane could be, for example, air in a microfluidic channel, a liquid metal, oil, or other fluid that may not mix with either the working or payload fluid.

FIG. 2B depicts an embodiment of a cross-sectional view of the inner assembly 204. The electroosmotic element 206 may be supported by the holder 212, and electrodes 208 may be on either side of the electroosmotic element 206 and extend out of the inner assembly 204. The electrodes 208 may extend to receive a voltage and deliver it to the electroosmotic element 206. In this embodiment, the working fluid 214 may be enclosed within the bellows 210 to drive their movement. In some further embodiments, a sealant may further be utilized with the pump(s) or an implant associated therewith to further ensure that the working fluid 214 does not leak out and/or mix with any of the medical contents being pumped in to the human body or critical organ. In an exemplary embodiment the sealant may be a material unaffected by the chemical properties of the working fluid 214.

Figure 3:
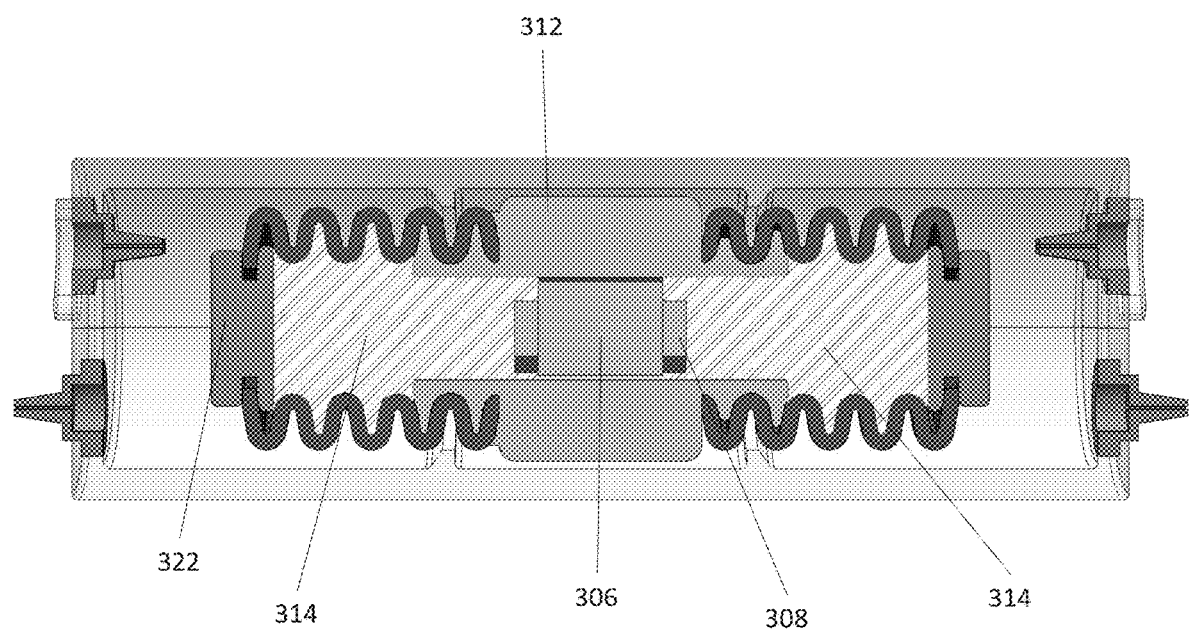
FIG. 3 shows a cross-sectional view of an exemplary embodiment of the bidirectional electroosmotic pump highlighting the working fluid.

FIG. 3 depicts a cross-section view of an embodiment of a bidirectional electroosmotic pump 300. It may be appreciated that the elements may be formed out of any of a variety of biocompatible materials or combinations thereof, based on implementation and use within, for example, the human body. In this figure, the working fluid 314 is displayed with cross-hatching. The working fluid 314 may include a variety of fluids based on electrical conduction properties and long-term ability to prevent bubble formation secondary to molecular electrolysis and/or repetitive conduction. Types of working fluids 314 may depend on the ability to be moved by electroosmosis and could include, for example deionized water, ethanol, or DMSO. In other embodiments the working fluid 314 may be another polar fluid compatible with the pump materials that may be used, and in some embodiments compatibility may require the working fluid 314 to be particle free, as particles in the working fluid 314 may clog the pores in the EOE, which may prevent the movement of the working fluid, which may reduce flow rate or cease pumping entirely 314. In some embodiments the fluid may have a viscosity similar to water, and the fluid may be sterilized with a method compatible with the pump. For example, with ethylene oxide sterilization. The working fluid 314 may surround the electroosmotic element 306 and the electrodes 308. The working fluid 314, electroosmotic element 306 and electrodes 308 may all be confined within the holder 312 and be capped 322.

Figure 4:
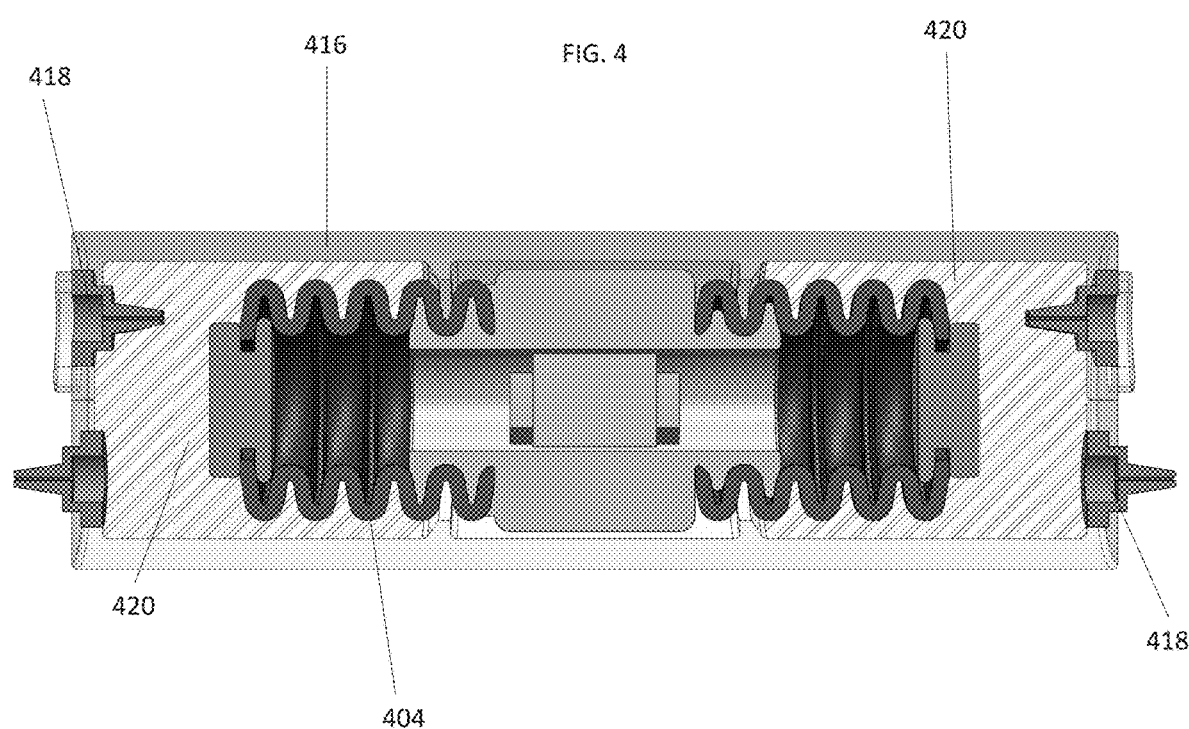
FIG. 4 shows a cross-sectional view of an exemplary embodiment of the bidirectional electroosmotic pump highlighting the payload fluid.

FIG. 4 depicts a cross-sectional view of an embodiment of a bidirectional electroosmotic pump 400. It may be appreciated that the parts may be formed out of any of a variety of biocompatible materials or combinations thereof, based on implementation and use. In this figure, the payload fluid 420 is displayed with cross-hatching. Possibilities for the payload fluid 420 may include a specific fluid which is time-stable and able to not degrade and remain at constant volume without evaporating or electrolyzing over time at normothermic conditions (for example, 98.6 degrees Fahrenheit). The payload fluid 420 may be able to flow through sub 1.5 mm channels and may include any water-based fluid or fluid with similar properties. The payload fluid 420 may be stable at human body temperature, have low viscosity, be compatible with any material used in the system, and/or be injectable through a device refill system. The payload fluid 420 may surround the inner assembly 404 and itself can be enclosed by the external housing 416. A series of valves 418 may facilitate the flow of the payload fluid 420 in and out of the pump 400. In an embodiment, the external housing 416 may include four valves 418, two of which may direct the payload fluid 420 outward, two which may bring the payload fluid 420 in. It may be understood that other embodiments may utilize different numbers of valves and/or orientations of the valves. For example, in other embodiments, only two valves may be used, or more than four plugs may be used. Further, it may be appreciated that valves 418 may provide for an additional level of safety for and control of drug delivery in instances where too little or too much drug delivery can cause severe adverse events including brain injury, spinal cord paralysis, tumor recurrence, and/or patient death. Thus, in such embodiments, valves 418 may be monitored by some associated sensors and/or controlled such as to prevent any over- or under-delivery of medicine.

Figure 5:
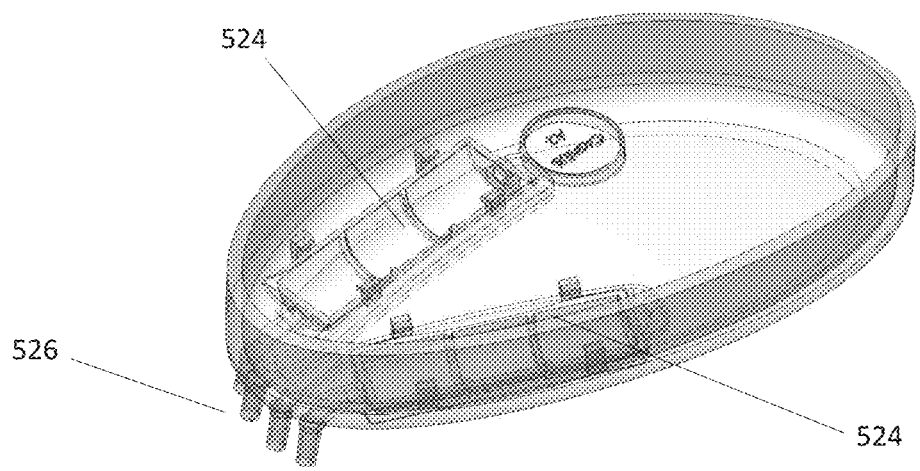
FIG. 5 shows an exemplary embodiment of an implant device embedded with the bidirectional electroosmotic pump(s).

FIG. 5 depicts an embodiment of an implant device 500 that can be used to deliver medicine. It may be appreciated that the elements may be formed out of any of a variety of biocompatible materials or combinations thereof, based on implementation and use. In this embodiment, the device may contain two bidirectional pumps 524 in parallel connected to four exit catheters 526 which may extend out of the device. The pump arrangement can be reconfigured based on the device design and goals; and may contain a varying number of pumps and exit port catheters based on clinical application and/or final size requirements. Further, in the embodiment of FIG. 5, the arrangement of the bidirectional pumps 524 may provide for maximized multi-catheter pump flow and minimized overall footprint, thereby improving patient outcomes when implanted in the human body. Further, such an arrangement of pumps 524 may also mitigate risks for visible deformity status post-operatively (i.e. a visible pump on a person's head when receiving brain medicine through a pump delivery system). The pumps may be configured in a way to transmit fluid from the device. The catheters 526 may be formed by a flexible, biocompatible material to carry fluid from the device and to the target area. The catheters may be able to, for example, allow for 0.5-5 μl/min of fluid to pass through them. It may be understood that the number and type of the exit port can be adjusted based on need. Having multiple catheters may be advantageous over singe-catheter devices in that there is additional duplicity of medicine delivery in case a catheter blockage was to occur (i.e., with a one catheter device system a blockage formation equates to no medicine delivery versus a two catheter device system which may still continue to deliver medicine).

In an exemplary embodiment the device may also include a battery. The battery may be ideal when deemed MRI compatible in line with the rest of the device. In the embodiments, any battery or battery system may have a fixed life span, or, have a rechargeable battery system which may use wireless charging. The pump may be powered by, for example, any battery with a long enough life span, or a wirelessly rechargeable power source, both of which may deliver power to the system and contain minimal ferromagnetic materials.

In an alternative embodiment, a photo-sensing system may be an alternative method of sensing the state of the pump. The photo-sensing system may use infrared (IR) LEDs and phototransistors to sense the state of a membrane separating the working and payload fluids. An alternative shape may be utilized, for example a shape consisting of a dome made from silicone or other elastic material. The bidirectional pump may be able to utilize such an LED-phototransistor combination to detect how deformed or compressed the rubber dome is at any point in time and therefore detect the status of the pump's pumping cycle. For example, if the elastic dome is extended towards the EOE, the phototransistor may receive less IR light from the LED. Vice versa, when the dome is completely collapsed, the phototransistor may receive more IR light from the LED.

Figure 6:
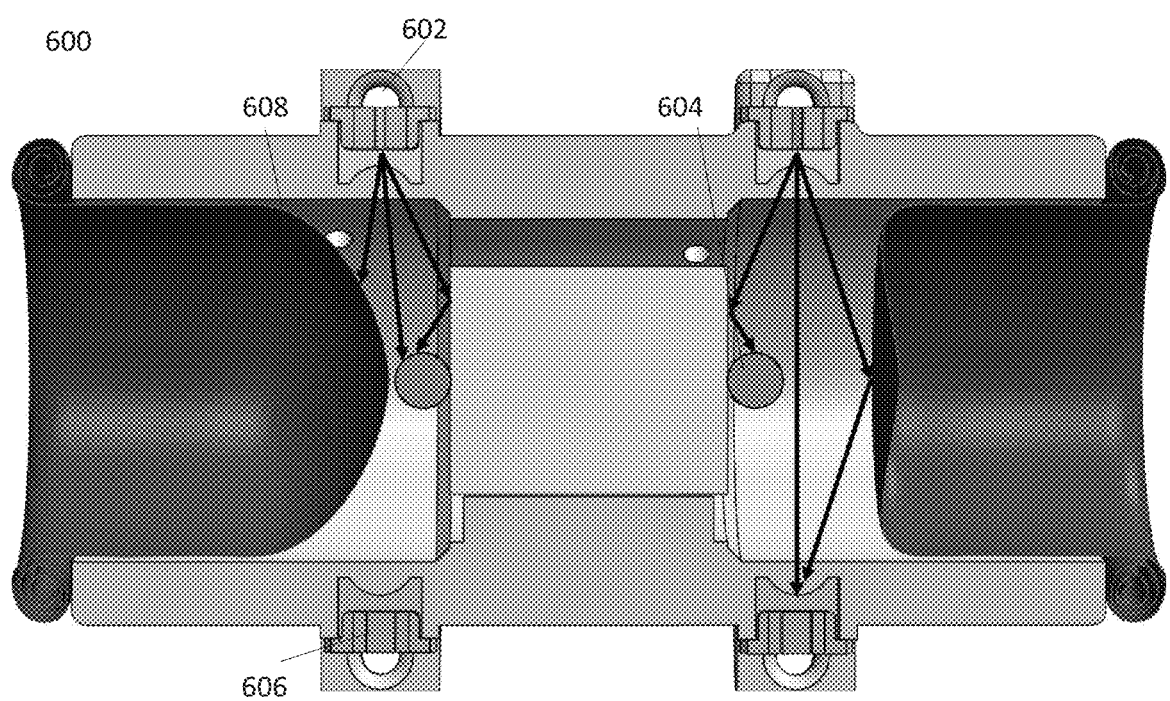
FIG. 6 shows a cross-section of an exemplary embodiment of a photo-sensing mechanism.

FIG. 6 depicts a cross-section of an exemplary embodiment of a photo-sensing mechanism 600. The photo-sensing mechanism 600 may have an IR LED 602 which transmits light across the diameter of the pump assembly. Further, there may be a platinum wire 604 which provides a barrier for the light to pass through to fully close the light sensing circuit. The photo-sensing mechanism 600 may also have an IR phototransistor 606 that detects deformation of a rubber dome 608. The rubber dome 608 may be dipped in another material, for example graphene, on the internal and/or external faces. In other embodiments the dome 608 may instead be made of fluorinated carbon-based synthetic rubber (FKM), fluorosilicone, or any other elastic material. The rubber dome 608 may be able to be deformed at the tip and collapse into itself. This motion may allow for an optical path between the LED 602 and the phototransistor 606. By determining whether the path exists or is blocked the state of the bellows may be determined.

In other embodiments, as an alternative to using solid material to separate the working and payload fluids, a fluid membrane may be used. The fluid membrane may be, for example, a liquid metal, oil, or any other fluid that will not be absorbed into the working or payload fluid. This fluid membrane may achieve the same interaction as a solid barrier provided by a metal bellow or rubber dome. The fluid membrane may be moved, therefore moving the payload fluid, by, for example, being oscillated by the working fluid movement through the electroosmotic element (EOE). Oscillations of the fluid membrane may be achieved in a way that prevents any form of negative auditory feedback to the patient following human body implantation. This may be critical, for example, in embodiments where the implantable bidirectional pump sits within a skull-soft tissue temporal space in close proximity to the patient's ear.

In an exemplary embodiment the components may be bonded together using a one-part, biocompatible, room temperature vulcanizing (RTV) silicone. In other embodiments, the components may be bonded using, for example but not limited to, laser welding, spot welding, glass-metal seals, ultrasonic welding, epoxies, or UV adhesives.

In an exemplary embodiment, the bidirectional electroosmotic pump(s) may be integrated into a medical implant case. The case may be designed to match the human body shape constraints (i.e. using well accepted normative data) related to its final anatomical destination; so that it can be provided to the physician/surgeon as an "off-the-shelf" solution. This may also allow for outlet pathways to exit ports for the payload fluid to also be embedded into the medical implant case. The pump(s) may be connected by, for example, manifolds, silicone tubing, and/or fitting pieces.

Figure 7A:
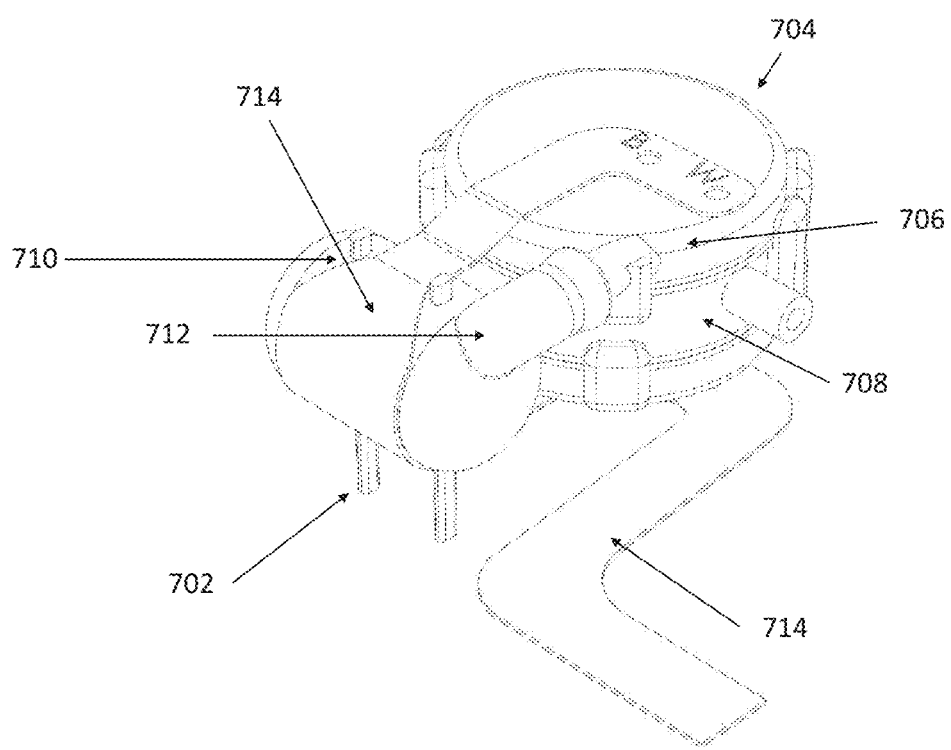
FIG. 7A shown an exemplary alternative embodiment of a bidirectional electroosmotic pump.

FIG. 7A depicts an exemplary alternative embodiment of a bidirectional electroosmotic pump. The exemplary EOP 700 design may have one or more electrodes 702 that may power the EOP 700. The one or more electrodes 702 may be made of, for example, platinum. The EOP 700 may further have an EOP bellows housing 704 which may further have an outer housing 706 and an inner housing 708. The bellow housing 704, outer housing 706, and inner housing 708 may be made of, for example, titanium, another metal, polyphenylene sulfide (PPS), other plastics, other polymers, and/or any other materials known in the art. In some embodiments the outer housing 706 and the inner housing 708 may be made of the same material while in others they may be made of different material. The inner housing 708 and outer housing 706 may be connected through, for example, welding, ultrasonic welding, or an adhesive. The EOP 700 may further have an EOE housing 710. The EOE housing 710 may be connected to the bellows housing 704 by a connector 712. The EOE housing 710 may be made of, for example, polymers, titanium, another metal, glass, and/or ceramics. A working fluid 764 may further be contained in the EOE housing 710. It may be understood that the working fluid may be able to move between the EOE housing 710 and the EOP bellows housing 704 via the connector 712. The EOP 700 may further be connected to a pump management printed circuit board (PCB) 714 which may be connected to and control the electrodes 702 and/or to bellows sensing wires 726.

Figure 7B:
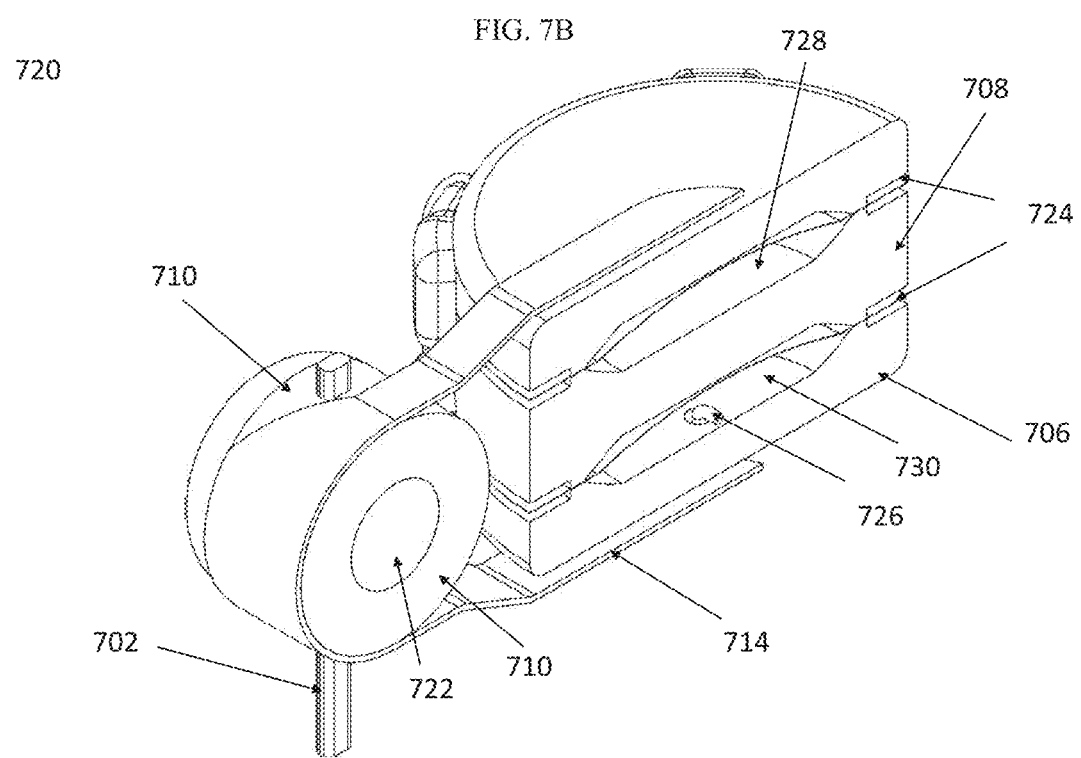
FIG. 7B shows a cross-sectional view of the exemplary alternative embodiment of the bidirectional electroosmotic pump.

FIG. 7B depicts a cross-sectional view 720 of the exemplary alternative embodiment of the EOP 700. Within the EOE housing 710 there may be an electroosmotic element 722. The electrodes 702 may be attached to the electroosmotic element through, for example, insert molding to pass electric charge to the electroosmotic element face, which may be, for example, platinum paste. The electroosmotic element 722 may be a material such as ceramic, that when voltage is applied to the electroosmotic element 722 through the electrodes 702 the working fluid 764 is moved. The electroosmotic element 722 may be porous, which may enable the working fluid to flow through, causing the electroosmotic effect that drives the bidirectional electroosmotic pump. In an exemplary embodiment, the electroosmotic element 722 may be, for example, a porous ceramic body. In other embodiments, the electroosmotic element 722 may be other materials, including but not limited to various dielectrics such as sintered glass, silica, and/or alumina. When the voltage being applied to the electrodes 702 is alternated between a first polarity and a second opposite polarity, a reciprocating fluid motion may be generated through the movement of the working fluid 764. This movement may help control movement of bellows 724, for example by moving via the connector 712 into one or more working fluid chambers 728. The bellows 724 may be, for example, a titanium foil that is formed into a dome shape and deforms under pressure. The bellows 724 may be connected to the EOP bellows housing via, for example, welding. The movement of the bellows 724 may be detected and recorded by one or more bellows sensors 726 which may be contained within one or more of the working fluid chambers 728 and/or payload fluid chambers 730. The bellows sensors 726 may be attached using, for example, epoxy. The bellows sensors 726 may be electrodes and may work by, for example, sensing an electrical connection created when the bellows 724 deform and contact the bellows sensors 726. When the bellows sensors 726 sense such a connection or otherwise determine that the bellows have been deformed, the electrodes 702 may switch polarity to the opposite polarity, which may begin a new pumping cycle.

Figure 7C:
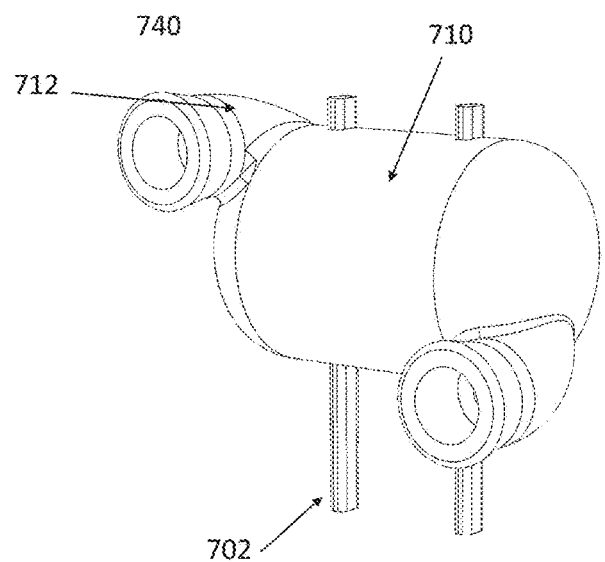
FIG. 7C shows an exemplary inner assembly for the exemplary alternative embodiment of the bidirectional electroosmotic pump.
Figure 7D:
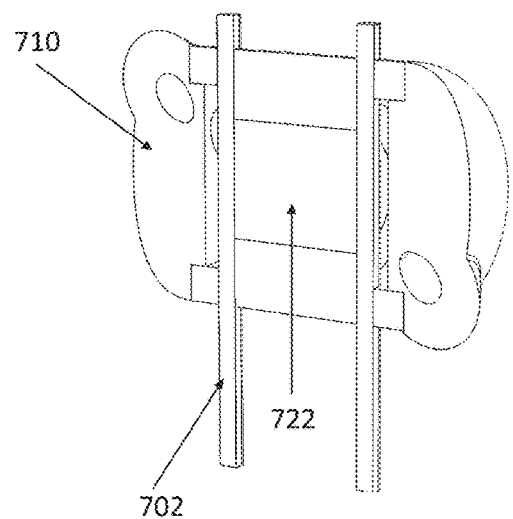
FIG. 7D shows a cross sectional view of the exemplary inner assembly for the exemplary alternative embodiment of the bidirectional electroosmotic pump.

FIGS. 7C and 7D depict an exemplary inner assembly 740 of the electroosmotic element housing 710 for the exemplary alternative embodiment of the bidirectional electroosmotic pump 700.

Figures 7E, 7F:
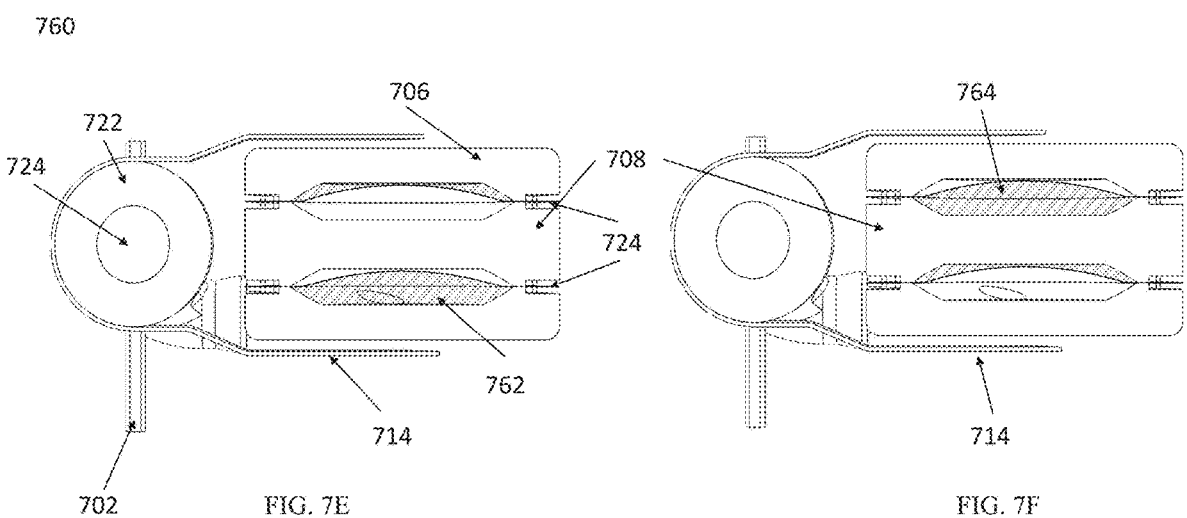
FIG. 7E shows a cross sectional view of an exemplary bellows assembly for the exemplary alternative embodiment of the bidirectional electroosmotic pump.
FIG. 7F shows another cross sectional view of an exemplary bellows assembly for the exemplary alternative embodiment of the bidirectional electroosmotic pump.

FIGS. 7E and 7F depict an interior view of the exemplary alternative embodiment of the bidirectional electroosmotic pump 760. Initially, the payload chamber 730 may be filled with a payload fluid 762, where the payload fluid 762 may be, for example, saline, an MRI tracer such as gadolinium, a medication such as topotecan, another medication known to be a safe and effective anti-tumor medicine in the setting of high grade glioma, or another fluid with clinical benefits known in the art. In some embodiments, the payload fluid may be a combination of fluids, for example, an MRI tracer and a medication, or two or more medications, where the fluids are compatible with each other. As electroosmosis is used to move the working fluid 764, the one or more working fluid chambers 728 may be filled, causing the bellows in the payload chamber 730 to restrict and expand, thereby pushing some of the payload fluid 762 out to be delivered.

FIG. 7G depicts an EOP assembly utilizing the exemplary alternative embodiment of the EOP 780. The EOP 700 may be connected with one or more check valves 782 via one or more joints 784. The one or more joints 784 may facilitate movement of the payload fluid 762 to the check valves 782. In an exemplary embodiment, as the reciprocating motion of the bellows intakes the payload fluid 762, the check valves 782 may allow fluid to pass through from the reservoir and the outlet valves may help prevent backflow. Backflow would be dangerous in instances of medicine reflux, and therefore, may be avoided using a valve-assisted design such as this. When the bellows 724 expel the payload fluid 762 the inlet valve may prevent backflow while the outlet valve dispenses the payload fluid 762, for example, through one or more catheters.

Figure 8:
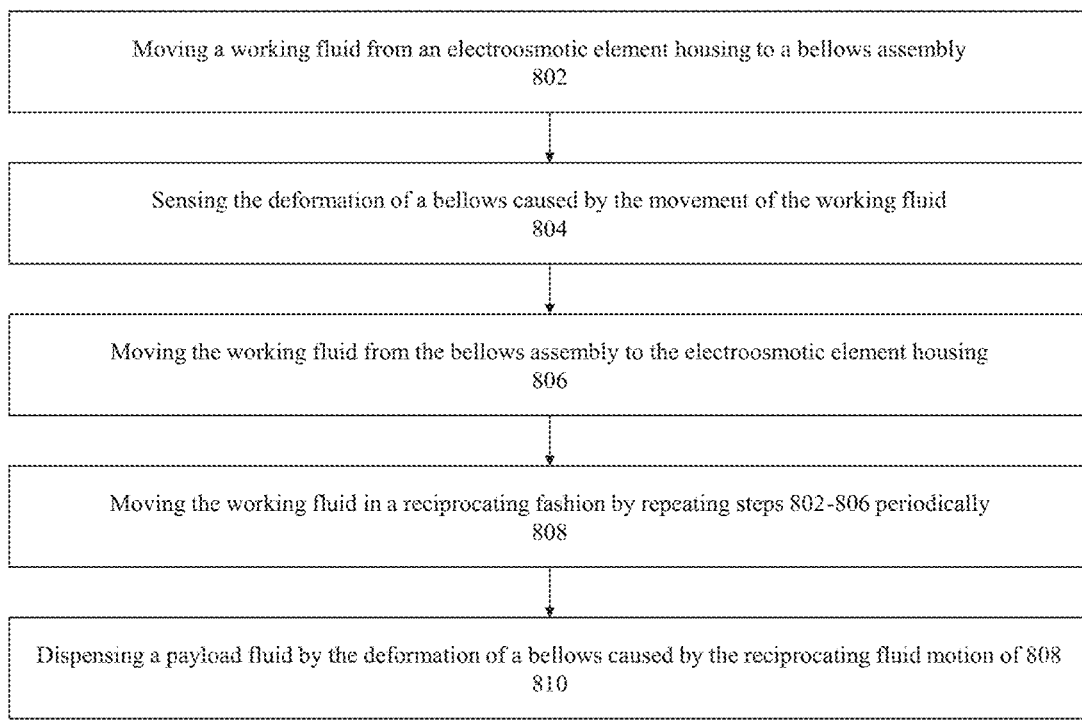
FIG. 8 shows an exemplary method for using a bidirectional electroosmotic pump assembly.

FIG. 8 depicts an exemplary method for using a bidirectional electroosmotic pump 800. For the sake of example, the method will be shown with reference to the bidirectional electroosmotic pump 700 described in FIGS. 7A-7G, however, in other embodiments the method 800 may be used with other electroosmotic pumps such as those described above, or other embodiments not described herein. In a first step 802, the working fluid 764 may be moved from the electroosmotic element housing 710 to the bellows assembly 704 by applying a first polarity electric potential to the one or more electrodes 702. This may cause the bellows 742 to deform as the working fluid 764 begins to fill the one or more working fluid chambers 728. In a second step 804 the deformation of the bellows 742 may be sensed by the one or more bellows sensors 726 and communicated to other systems via the pump management PCB 714.

In a third step 806 the working fluid 764 may be moved back to the electroosmotic housing 710 from the bellows assembly 704 by switching the polarity of the electric potential being applied to the one or more electrodes 702 to the opposite polarity. The switch may be done automatically based on the sensing mechanism described in step 804. In a fourth step 808, steps 802-806 may be repeated periodically in order to create a reciprocating movement of the working fluid 764, which may allow the bellows 742 to move at a continuous rate. The periodic rate may be based on the sensing mechanism, and the sensing mechanism may have a programmable delay to control the switching time span. In a final step 810, the payload fluid 762 may be dispensed from the bidirectional electroosmotic pump based on the movement of the bellows. By using an embedded software technology platform, the time interval of each sensing mechanism and pump adjustment may be adjusted wirelessly and remotely at any timepoint; thereby changing hourly, daily, weekly, monthly, and/or yearly quantities of medicine delivery through different instantaneous active flow rates, average flow rates based on swept volume, and/or infusion schedules. In an exemplary embodiment the pump may have a mirrored design which causes the sides of the pump to alternate which step of FIG. 8 they are on. For example, if the first pump is on step 802 the second half of the pump may simultaneously be on step 806.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art. Additionally it may be understood that parts or aspects described in one embodiment may likewise be used in other embodiments where appropriate.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A bidirectional pump for medical implants, comprising:
   an electroosmotic element housing comprising:
      an electroosmotic element; and
      one or more electrodes which pass through the electroosmotic element;
   a bellows assembly comprising:
      a payload fluid configured to be dispensed from the bidirectional pump; and
      a connector which allows for movement of a working fluid from the electroosmotic element housing to the bellows assembly and back from the bellows assembly to the electroosmotic element housing based on an electrical current being applied to the one or more electrodes.

2. The pump of claim 1, wherein the bellows assembly includes a bellows housing made of one of titanium, polyethylene terephthalate (PET), or polyphenylene sulfide.

3. The pump of claim 1, further comprising:
   one or more check valves; and
   one or more joints connecting the one or more check valves to the bellows assembly.

4. The pump of claim 1, further comprising a pump management PCB that is connected to both the electroosmotic element housing and the bellows assembly;
   wherein the pump management PCB detects a pumping cycle through one or more bellows sensors.

5. The pump of claim 1, wherein the electroosmotic element is made of one or more of ceramic and platinum.

6. The pump of claim 5, wherein the electroosmotic element is a porous ceramic body with porous platinum paste applied to two faces of the ceramic body;
   the one or more electrodes are attached to the electroosmotic element through insert molding; and electric current is passed to the electroosmotic element from the one or more electrodes through the porous platinum paste.

7. The pump of claim 1, wherein the working fluid is a particle free polar fluid with viscosity of about that of water.

8. The pump of claim 1, wherein the payload fluid is one or more of saline, an MRI tracer, and a fluid with clinical benefits.

9. A bidirectional pump for medical implants, comprising:
an electroosmotic element housing comprising:
an electroosmotic element; and
one or more electrodes which pass through the electroosmotic element;
a bellows assembly comprising:
a bellows housing;
two or more bellows within the bellows housing; and
one or more bellows sensors within the bellows housing;
wherein the bellows assembly is configured to dispense one or more fluids.

10. The pump of claim 9, wherein the bellows housing is made of one of titanium, polyethylene terephthalate (PET), or polyphenylene sulfide.

11. The pump of claim 9, wherein the two or more bellows are made of titanium foil.

12. The pump of claim 11, further comprising a pump management PCB that is connected to both the electroosmotic element housing and the bellows assembly;
wherein the pump management PCB detects a pumping cycle through the one or more bellows sensors.

13. The pump of claim 9, wherein the electroosmotic element is made of one or more of ceramic and platinum.

14. The pump of claim 13, wherein the electroosmotic element is a porous ceramic body with porous platinum paste applied to two faces of the ceramic body;
the one or more electrodes are attached to the electroosmotic element through insert molding; and
electric current is passed to the electroosmotic element from the one or more electrodes through the porous platinum paste.

15. A method for delivering fluid through an implanted medical device, comprising:
moving a working fluid from an electroosmotic element housing to a bellows assembly by applying a first polarity electric current to an electroosmotic element through one or more electrodes which pass through the electroosmotic element causing a deformation of a bellows;
moving the working fluid from the bellows assembly to the electroosmotic element housing by applying an opposite polarity electric current to the one or more electrodes after detecting the deformation of the bellows;
moving the working fluid in a reciprocating fluid fashion by periodically repeating the applying of the first polarity electric current and the opposite polarity electric current to the one or more electrodes; and
dispensing a payload fluid by the deformation of the bellows caused by the reciprocating fluid motion of the working fluid.

* * * * *